(12) United States Patent
Alvaro Galue

(10) Patent No.: US 11,260,077 B2
(45) Date of Patent: Mar. 1, 2022

(54) PROCESS FOR OBTAINING A SPRINKLING COMPOUND OF MICROVASCULAR ENDOTHELIAL SKIN CELLS AND MESENCHYMAL STEM CELLS AND METHOD OF APPLICATION FOR TISSUE REGENERATION

(71) Applicant: Eduardo Alvaro Galue, Nuevo Leon (MX)

(72) Inventor: Eduardo Alvaro Galue, Nuevo Leon (MX)

( * ) Notice: Subject to any disclaimer, the term of this patent is extended or adjusted under 35 U.S.C. 154(b) by 825 days.

(21) Appl. No.: 15/758,101

(22) PCT Filed: Sep. 6, 2016

(86) PCT No.: PCT/MX2016/000091
§ 371 (c)(1),
(2) Date: Oct. 24, 2018

(87) PCT Pub. No.: WO2017/043953
PCT Pub. Date: Mar. 16, 2017

(65) Prior Publication Data
US 2019/0046573 A1 Feb. 14, 2019

(30) Foreign Application Priority Data
Sep. 7, 2015 (MX) .................... MX/a/2015/011801

(51) Int. Cl.
| | |
|---|---|
| *A61K 35/28* | (2015.01) |
| *A61K 9/70* | (2006.01) |
| *A61P 17/02* | (2006.01) |
| *C12N 5/071* | (2010.01) |
| *C12N 5/0775* | (2010.01) |
| *A61K 35/36* | (2015.01) |
| *A61L 27/38* | (2006.01) |
| *A61K 35/44* | (2015.01) |
| *A61L 27/60* | (2006.01) |
| *A61L 27/50* | (2006.01) |

(52) U.S. Cl.
CPC ............ *A61K 35/28* (2013.01); *A61K 9/7015* (2013.01); *A61K 35/36* (2013.01); *A61K 35/44* (2013.01); *A61L 27/3808* (2013.01); *A61L 27/3834* (2013.01); *A61L 27/3886* (2013.01); *A61L 27/50* (2013.01); *A61L 27/60* (2013.01); *A61P 17/02* (2018.01); *C12N 5/069* (2013.01); *C12N 5/0663* (2013.01); *C12N 5/0668* (2013.01); *C12N 5/0698* (2013.01); *A61L 2400/06* (2013.01)

(58) Field of Classification Search
None
See application file for complete search history.

(56) References Cited

FOREIGN PATENT DOCUMENTS

| | | |
|---|---|---|
| ES | 2377962 | 4/2012 |
| WO | WO2015119491 | 8/2015 |

OTHER PUBLICATIONS

Falanga, et al. (2007) "Autologous Bone Marrow-Derived Cultured Mesenchymal Stem Cells Delivered in a Fibrin Spray Accelerate Healing in Murine and Human Cutaneous Wounds", Tissue Engineering, 13(6): 1299-1312.*
Damien G. Harkin et al. "Optimized delivery of skin keratinocytes by aerosolization and suspension in fibrin tissue adhesive". Wound Repair and Regeneration, Mosby-Year Book, St. Louis, MO, US Jan. 5, 2006, vol. 14 No. 3, pp. 354-363, ISSN 1067-1927.

* cited by examiner

*Primary Examiner* — Robert M Kelly
(74) *Attorney, Agent, or Firm* — Defillo & Associates, Inc.; Evelyn A Defillo

(57) ABSTRACT

The invention relates to a process for obtaining a cellular sprinkling compound and to the respective method of application to provide a therapeutic treatment for skin injuries, based on the implantation, by sprinkling and/or spraying, of human mesenchymal stem cells and microvascular endothelial cells that have been pre-expanded in vitro and resuspended in a regenerative solution for cellular implantation of biocompatible biomaterials. The solution is formed by blood plasma rich in growth factors obtained from the patient to be treated and, in some cases, by medical-grade type I collagen and by medical-grade hyaluronic acid, which potentiates the regeneration, re-epithelialization, and reconstruction of skin tissue.

13 Claims, No Drawings

PROCESS FOR OBTAINING A SPRINKLING COMPOUND OF MICROVASCULAR ENDOTHELIAL SKIN CELLS AND MESENCHYMAL STEM CELLS AND METHOD OF APPLICATION FOR TISSUE REGENERATION

CROSS REFERENCE TO RELATED APPLICATION

This application is a national stage entry of PCT/MX2016/000091 filed Sep. 6, 2016, under the International Convention claiming priority over Mexican Patent Application No. Mx/a/2015/011801 filed Sep. 7, 2015.

OBJECTIVE OF THE INVENTION

The objective refers to a process of obtaining a cellular spraying compound in a regenerative solution and its respective application method to generate a regenerative therapeutic treatment for cutaneous lesions, which is based on implantation by spraying and/or pulverizing vascular micro endothelial cells of the human skin obtained from autologous tissue and allogeneic tissue of a newborn prepuce or an adult skin and from mesenchymal stem cells obtained from various tissues both autologous and allogeneic, which are preferably: an adipose tissue, or the peripheral blood, or the bone narrow or of the amniotic fluid, or an umbilical cord blood, or a dental pulp; pre-expanded in vitro under sterile conditions of a clean room (ISO-4 to ISO-6) and re-suspended in a regenerative solution of cellular implantation composed of a combination of biocompatible and biodegradables biomaterials mainly containing a heme derived from a plasma rich in platelets (plasma rich in growth factors) and fibrinogen that potentiate the therapeutic effect of the cells in the tissue repairing. This effect brings as a result a rapid re-epithelization and regeneration of the cutaneous wound.

The regenerative solution functions as a cellular implantation vehicle which has the function of transporting, protecting, encapsulating, and facilitating the implantation of both cells on the lesion and is mainly constituted by blood plasma rich in growth factors obtained from the patient to be treated, and in turn it can be combined with type I collagen and hyaluronic acid both of medical grade at different concentrations.

The therapeutic application of all the components of this cellular spraying compound and its regenerative solution potentiates the treatment of implanted cells by the formation of new healthy tissue promoting a rapid re-epithelization and regeneration of the wound in a short time.

The process of obtaining a cellular spraying compound and its method of application by spraying and/or pulverizing without damaging the cells for a regenerative therapeutic treatment of cutaneous lesions, represents an innovative biomedical technology with a high degree of effectiveness in the regeneration, re-epithelization and reconstruction of the cutaneous tissue increasing the morbidity and recovery of the patient, preventing their wounds from being exposed to microbial infections and delayed recovery. Added to this, other advantages of obtaining a cell spray composition and its application by spraying and/or pulverizing on skin lesions is that it neutralizes the body healing process itself, since it stimulates the repair and the regeneration tissular of the damaged tissue. The consequence of the activation of the healing process of the body with the traditional recovery methods of a burned patient has as a result that the body inflammatory system to begin to make a muscular contraction in the damaged tissue that brings as a consequence a lack of recovery of the tissue functionality, the presence of fibrotic tissue in the cutaneous lesion, an acute inflammatory process present in the recovery of the patient, a long recovery time, and the morbidity of the patient, trauma sequels, formation of keloid scars in the scar tissue and above all it represents a high public and private expense in bed days for the recovery of these patients.

BACKGROUND OF THE INVENTION

Currently, the use of allogeneic grafts and xeno transplants limits the skin regeneration due to inflammatory processes that originate from the immunological rejection that involves the use of the donor skin and the use of animal skin. This causes the low availability of said biological material for the treatment of cutaneous wounds, and there is the disadvantage of the susceptibility to infections. Currently, there are patents for printing techniques of living human cells called Bioprinting where mesenchymal stem cells and microvesicular endothelial cells are printed on cutaneous wounds. This technique is based on mechanically depositing by means of a robotic arm (with the freedom to move in the 3-dimensional axes) autologous cells on the wound. In addition to this, we can find dermal substitutes based on the in vitro culture of human microvascular endothelial cells on decellularized skin matrices of bovine origin. Its use is based only on the increase in the healing time of the wound by transplanting this decellularized matrix of bovine origin with human microvascular endothelial cells previously planted on its surface.

However, in addition to using an animal origin product (decellularized matrix) that is not 100% compatible with the human being, the use and transplantation of this product is based only on increasing the use of epithelization and regeneration of the wound and omitting the regeneration of the functionality of said skin, to create again the pigmentation and hair induction. Added to this, a severe trauma to this organ (skin) can cause partial or incomplete regeneration and atrophy by using these meshes with microvascular endothelial cells and a total lack for the generation of color and hair. Another approach to the epithelization and wound regeneration that has been developed in the laboratory is based on the in vitro culture of human keratinocytes from the prepuce of newborns on layers of fibroblasts (known as 3T3 cell line) from mouse embryos with a high degree of proliferation. This system created in vitro has disadvantages such as the low production of the extracellular matrix of the biograft created, a two-dimensional size very limited in thickness and support to cover the damaged area as a protective barrier to the wound, a low regeneration of the functionality of the skin during the healing of the wound (pigmentation and hair induction) and the use of animal cells for its production.

Currently, a process for generating a cellular spraying compound based on in vitro culture of human fibroblasts and combined human keratinocytes in autologous platelet-rich plasma obtained from the patient to be treated can be found with the patent application MX/a/201/001356 for the treatment of skin sessions such as burn, diabetic ulcers, and tissue reconstruction. In turn, this application entered into the patent cooperation treaty can also be found with application PCT/MX2015/000001. Also, we can mention the patent application MX/a/2015/07577 to which is a process of obtaining a compound for cellular spraying of mesenchymal stem cells and human microvascular endothelial cells in a regenerative solution and its method of application as a therapeutic agent of skin lesions. In all the above-mentioned applications of the present inventor, and the present invention originates from these patent applications, wherein the present invention describes substantial improvements not described in the aforementioned as the incorporation of mesenchymal stem cells and microvascular endothelial cells to the spray compound.

This new cellular combination will originate the formation of all damaged tissues from the implantation of mesenchymal stem cells capable of differentiating into different mesodermal tissues including dermis, epidermis and blood vessels. However, the novel incorporation of microvascular endothelial cells results in neovascularization of the new tissue, early angiogenesis and a new and rapid formation of capillaries and blood vessels for early irrigation of the formed tissue.

DETAILED DESCRIPTION OF THE INVENTION

The present invention relates to a process for obtaining a cellular spraying compound comprised of two components of constant simultaneous application by spraying/pulverizing, where the first component is composed of microvascular endothelial cells of skin and mesenchymal stem cells obtained from various tissues, wherein the cells in preparation, encapsulated, in mixture, or in combination with biodegradable biocompatible biomaterials natural and/or synthetic to be implanted temporarily, continuously, or systemically in lesions, traumas or cutaneous defects to generate a rapid re-epithelization and regeneration of the cutaneous tissue by forming a new extracellular matrix, in a short period of time and in turn promote the formation of fibrotic tissue; which is based on the implantation of skin microvascular endothelial cells and mesenchymal stem cells pre-expanded in vitro for a period of time and resuspended in a regenerative solution of cellular implantation composed mainly of platelet-rich plasma, where this compound can be mixed or not with collagen type 1 and hyaluronic acid to potentiate the repair effect of the compound.

Optionally, the use of mesenchymal stem cells can be substituted with the use of fibroblasts and keratinocytes in a 1:1 ratio with the microvascular endothelial cells of the skin in the first cellular spraying component.

The microvascular endothelial cells of the skin and the mesenchymal stem cells that make up this cellular spraying compound are cells isolated from autologous tissue or allogeneic tissue such as: adipose tissue, peripheral blood, bone marrow, amniotic fluid, dental pulp, prepuce of newborn or adult skin sample, where if the tissue is a donation must have characteristics of being free of any contagious infectious disease or history of hereditary disease and may also be isolated from a skin sample of the patient to be treated (autologous); where mesenchymal stem cells are specifically isolated from adipose tissue, or from peripheral blood, or from bone marrow or amniotic fluid, or umbilical cord blood, or from both autologous and allogeneic dental pulp, both of which are pre-expanded in vitro by a period of sterile conditions in a clean room (ISO-4 to ISO-6) for therapeutic use.

The regenerative solution that accompanies the process of spraying said cells is a solution composed of platelet-rich plasma with tissue repair factors obtained from a heme derived from blood tissue, which is based on the use of autologous (of the own patient) or allogeneic (from a platelet preserved cryo) that provides a potentization in tissue repair due to the presence of a platelet degranulation (PDGF) that releases growth tissue factors and repair which interact with cells of the cellular spraying compound for the formation of new healthy tissue, elimination of keloid scars, and recovery of its functionality in skin lesions. Said regenerative solution of the cellular spraying compound may or may not be combined with type I collagen and hyaluronic acid both medical and non-medical grade. In turn, the use of the heme derived from the platelet-rich plasma of the patient to be treated favors a decrease in the immunogenicity of the cells in case the aspersion compound carries in its mixture (allogenic) donation cells.

Subsequently, a second component or application compound which is based on a reaction reagent agent which is mainly comprised of human thrombin, $CaCl_2$, an antifibrinolytic agent and a saline solution or a phosphate buffer. This second component will interact with the molecules of the first component at the moment of being expelled simultaneously in the air by a spray nozzle to generate a polymerization of the components on the lesion or skin wound producing a gel layer in the wound covering the total wound thickness (deep) or partial (superficial). This cellular spraying compound is mechanically applied by means of a medical aerosolization device (FibriJet-Micromedics) or any other medical device that has simultaneous spraying/pulverization properties of two components or containers that can contain (1) the cellular spraying compound with the micro vascular endothelial cells, mesenchymal stem cells and a regenerative solution or transport medium mainly composed of plasma rich in plaques, collagen type 1, and hyaluronic acid and (2) the compound with the reaction cross-linking agent composed of human thrombin, $CaCl_2$, an antifibrinolytic agent, and a saline solution.

Also, it should present characteristics of constant and regulated supply of air or compressed oxygen with the capability to control the pressure ranges between 5 psi-35 psi, and with a nozzle to produce fine drops and thick drops of the cellular spraying compound according to the supply pressure of the air. This tissue regenerative compound results in a pulverization/aspersion of fine or thick drops of the regenerative solution of cellular implantation composed of a combination of biodegradable, biocompatible and biomaterials, containing inside the microvascular endothelial skin cells and autologous mesenchymal stem cells and/or allogenic and interacting in the air with the second component. As a result, the fine droplets or thick droplets will polymerize in the air by combining both components and will be deposited on the skin lesion to be repaired, forming a polymerized three-dimensional network (Gel) or biological cover that encapsulates, transports, protects, implants, and facilitates the application of mesenchymal stem cells and microvascular endothelial cells on the cutaneous wound.

The microvascular endothelial cells are cells that will originate a micro-vasculature in the injury in a shorter time. The mesenchymal stem cell is a cell that has the ability to differentiate into mesodermal layer tissues with proliferative, plasticity and self-renewal capabilities. The therapeutic use of this cell type results in the generation of new skin in lesions or cutaneous traumas in a relatively shorter time than the skin's own cells.

The mechanism of action of the cellular spraying compound is based on the uniform distribution on the wound of both components of the spraying compound to facilitate cell adhesion of skin microvascular endothelial cells and mesenchymal stem cells, creating an ideal environment for the formation of new extracellular matrix or a cutaneous tissue (re-epithelization and regeneration), generate or promote a biological coverage on the wound, protection of the wound to prevent water loss and protection for the susceptibility to infections.

Optionally, the cellular spraying compound can be replaced by mesenchymal stem cells by the use of fibroblasts and keratinocytes in a 1:1 ratio, which together with microvascular endothelial cells will provide the native structure of the skin to be repaired.

The regenerative solution or transport medium of the cellular aspersion compound comes from the patient's blood tissue (autologous platelets) or from a preserved cryoprobe of blood bank platelets, which, in turn, will bring and supply the wound with an autologous platelet degranulation (PDGF) for the release of tissue factors/slow growth (TGF, EGF, G-CSF, IGF, PDGF, VEGF, FGF, JL-8, KGF, CTGF, etc), cytokines and inflammatory signaling that provides a suitable cellular micro-environment and not only the implantation of the protein known as fibrinogen for the polymerization of both components. The implanted cells (skin microvascular endothelial cells) and mesenchymal stem cells have an interaction with proteins derived from the blood plasma (IgG, Albumin, etc.) of the regenerative solution stimulated an adherence and cellular configuration from the activation of the cascades of coagulation. The result of this process is an early cellular reorganization, remodeling, and re-epithelialization of the wound, causing the formation of a new ex-cellular matrix (epidermis-dermis) and avoiding the formation of fibrotic tissue resulting from muscle contraction.

This compound of cellular spraying of microvascular endothelial cells and mesenchymal stem cells or the use of fibroblasts plus keratinocytes in a 1:1 ratio enhances homeostasis, remodeling and regeneration through early re-epithelialization of the wound, re-organization of tissue, modulation of inflammation/pain, angiogenesis/neovascularization, high water uptake (hydration) and above all an early regeneration of the lesion from the production of new skin and thus avoid exposure to infections and trauma sequelae; which comprises the following steps:

a) Isolate the Mesenchymal Stem Cells of Fibroblasts Plus Keratinocytes and Microvascular Endothelial Cells From a Tissue Capable of Containing Cells.

Obtaining a sample of autologous or allogeneic tissue of at least 5 cc, from said tissue, it should be possible to isolate mesenchymal stem cells.

For a better understanding, but without limiting the current methods of obtaining samples, the stem cells can be isolated by any procedure known to those skilled in the art. Specifically, sufficient amounts of mesenchymal stem cells can be obtained from adipose tissue, peripheral blood, umbilical cord blood, dental pulp, and amniotic fluid. These tissues can be obtained by aspiration and/or biopsy (when appropriate) or after autopsy or by donation. Subsequently, wash a sample of adipose tissue at least 3 times with a phosphate salt solution (PBS) 1× containing 1%-10% v/v of a 100% v/v solution of antibiotic/antifungal 100×v/v. Then wash at least 3 times with a 1×PBS solution containing 1%-10% v/v antibiotic/antifungal. Preferably, the antibiotic/antifungal solution is streptomycin/penicillin. After washing the adipose tissue sample, let stand for at least 10 minutes so that the fat floats on the surface of the wash container.

Subsequently, under sterile conditions, to obtain with a sterile pipette the layer composed of blood remains and PBS 1× that is located under the adipose tissue layer in the wash container. Subsequently, this sub-layer is placed in a falcon tube and centrifuged for at least 10 minutes at 1,500-2,000 rpm to obtain a cell pellet. Subsequently, under sterile conditions, the supernatant is carefully decanted, and the pellet is resuspended in a red blood cell lysis solution composed of 160 mM of $NH_4Cl$ for at least 5 minutes at room temperature. After 5 minutes, centrifuge for at least 10 minutes at 1,500-2,000 rpm. The supernatant is decanted, and the cell pellet is resuspended with nutrient cell culture medium for mesenchymal stem cells, preferably DMEM (Dulbecco's modified Eagle medium) high in glucose (4500 mg/L), 25 mM Hepes, supplemented with 1%-10% v/v of a streptomycin-penicillin solution, 10-40% v/v of human autologous serum to obtain mesenchymal stem cells in suspension.

In sterile conditions, the mesenchymal stem cells are planted in suspension in a special bottle for cell culture and incubated at 37° C. with 95% relative humidity, 5% $CO_2$ and 20% $O_2$ for at least 1 day without moving the bottle. Also, the pellet can be resuspended with cell culture medium for mesenchymal stem cells, supplemented with 1% v/v streptomycin-penicillin 100×, 10-40% v/v fetal bovine serum pharmaceutical grade.

After, to wash the adipose tissue, it can also be isolated from the mechanical dissociation of the white adipose tissue with scissors or sharps object and incubating this dissociated tissue with a proteolytic enzyme, collagenase Type IA preferably, at a concentration not less than 0.8% w/v e incubate 37° C. moving by at least minus 1 hour.

Subsequently, the action of the proteolytic enzyme is neutralized by adding at least 50% of the total volume of the adipose tissue with nutrient cell culture medium for mesenchymal stem cells supplemented with 10-40% v/v of human autologous serum or supplemented with 10-40% v/v of fetal bovine serum pharmaceutical grade.

Subsequently, under sterile conditions, centrifuge for at least 5 minutes at 1,500-1,800 rpm. Subsequently, in sterile conditions, decant the supernatant and resuspend the cell pellet with nutrient cell culture medium for mesenchymal stem cells supplemented with 1% v/v streptomycin-penicillin 100×, 10-40% v/v of human autologous serum or supplemented with 10-40% v/v fetal bovine serum pharmaceutical grade. Centrifuge again for at least 2 times and for at least 5 minutes at 1,500-1,800 rpm and decant the supernatant.

Subsequently, in sterile conditions resuspend the cell pellet again with nutrient cell culture medium for mesenchymal stem cells supplemented with 1% v/v streptomycin-penicillin 100×, 10-40% v/v human serum autologous or supplemented with 10-40% v/v pharmaceutical grade fetal bovine serum and sow in a special bottle for cell culture and incubate at 37° C. with 95% relative humidity, 5% $CO_2$ and 20% $O_2$ for at least 1 day without moving the cell culture bottle.

For peripheral blood tissue, it is obtained by venipuncture, bone marrow by aspiration of the iliac crest and umbilical cord blood by venipuncture of the central vein of the umbilical cord. All these tissues are deposited under sterile conditions in a container with preferably anticoagulant, acid citrate dextrose, sodium citrate, EDTA or heparin.

Subsequently, tissue dilution is performed with 1:1 with PBS 1×w/v or 0.9% v/v saline. Subsequently, in a second 15 m falcon tube or 50 ml, the blood samples will be separated by the density gradient technique placing 50% of the total volume of the tube with an iso-osmotic medium with a density of 1.077 g/ml w/v that allows the mononuclear cells that are present in blood tissue to be isolated. Subsequently, under sterile conditions, it is carefully deposited at an angle of not less than 45 degrees and the walls of the tube falcon, the diluted blood tissue depositing it on the iso-osmotic medium that has a density of 1.077 g/ml. Subsequently, the tubes containing the diluted blood tissue are centrifuged over the iso-osmotic medium for at least 10 minutes at a revolution of 1,500-2,500 rpm.

Subsequently, the mononuclear cell layer concentrate is isolated from the peripheral blood tissue, bone marrow, umbilical cord by carefully aspirating the mononuclear cell layer and depositing it in sterile conditions in another sterile falcon tube. Subsequently, resuspend the mononuclear cell layer with DMEM nutrient medium (Dulbecco's modified Eagle medium) high in glucose (4500 mg/L), 25 mM Hepes, supplemented with 1% v/v streptomycin-penicillin 100×, 10-40% v/v human autologous serum or supplemented with 10-40% v/v and centrifuge at least 2 times and for at least 5 minutes at 1,500-2,000 rpm. Subsequently, under sterile conditions, the mononuclear cells are seeded in a special bottle for cell culture and incubated at 37° C. with 95% relative humidity, 5% $CO_2$ and 20% $O_2$, at least 1 day without moving the bottle.

From amniotic fluid is made under sterile conditions by the amniocentesis technique from week 16 of gestation.

Subsequently, in sterile conditions, the sample is centrifuged between 1,500-2,000 rpm for at least 5 minutes. Subsequently, the supernatant is discarded and resuspended the cell pellet with 5 ml of cellular nutrient medium of mesenchymal stem cells of amniotic fluid composed, preferably by DMEM-alpha (Dulbecco's modified Eagle medium-alpha) supplemented with 1% v/v of amino acid L-Glutamine, 10-40% serum patient autologous, 1% v/v of streptomycin-penicillin 100×, 18% v/v of special medium Chang B and 2% of special medium Chang C. Subsequently, sow in a special bottle for cell culture and incubate at 37° C. with 95% relative humidity, 5% $CO_2$ and 20% $O_2$ for at least 1 day without moving the bottle. Also, the same results are obtained if the cell pellet is resuspended in a cellular nutrient medium of mesenchymal stem cells of amniotic fluid, preferably composed of DMEM-alpha supplemented with 1% v/v of amino acid L-Glutamine, of 10-40% serum Fetal bovine embryo pharmaceutical grade, 1% v/v of streptomycin-penicillin, 18% v/v of special medium Chang B and 2% of special medium Chang C. Subsequently, sow in a special bottle for cell culture and incubate at 37° C. with 95% relative humidity, 5% $CO_2$ and 20% $O_2$ for at least 1 day without moving the bottle.

From dental pulp, it is obtained from a healthy tooth and in sterile conditions. Wash the extracted tooth by at least 3 times with a phosphate salt solution (PBS) 1× containing 1-10% v/v of an antibiotic/antifungal solution. Afterward, wash at least 3 times with a 1×PBS solution containing 1%-10% v/v antibiotic/antimicrobial. Preferably, the antibiotic/antifungal solution is streptomycin/penicillin. After washing the tooth, extract the pulp tissue from the tooth by means of a sharpshooter. Then wash in PBS 1× for at least 3 times and place in a mixture of an enzymatic solution of 4 mg/mL type IA collagenase and 2 mg/mL of dispase in a 1:1 ratio for 60 minutes at 37° C. The suspension obtained was filtered through a 70 μm cell filter. Subsequently, the resulting cell suspension was centrifuged for 6 minutes at 1,500-1,700 rpm and resuspended in cellular nutrient medium of mesenchymal stem cells preferably composed of DMEM (Dulbecco's modified Eagle medium) in glucose (4500 mg/L), 25 mM Hepes, supplemented with 1% v/v of streptomycin-penicillin 100×, 10-40% v/v of human autologous serum or supplemented with 10-40% v/v and centrifuge for at least 2 times and for at least 5 minutes at 1,500-2,000 rpm.

Subsequently, under sterile conditions, the mononuclear cells are seeded in a special bottle for cell culture and incubated at 37° C. with 95% relative humidity, 5% $CO_2$ and 20% $O_2$ for at least 1 day without moving the bottle.

For the isolation of microvascular endothelial cells, it is done by means of a newborn foreskin or skin sample obtained by dermatome, skin punch, or patient or cadaver biopsy.

Subsequently, wash the skin sample for at least 3 times with a 1× phosphate salt solution (PBS) containing 1%-10% v/v of a 100×v/v antibiotic/antifungal solution. Then, wash at least 3 times with a 1×PBS solution containing 1%-10% v/v antibiotic/antifungal. Preferably, the antibiotic/antifungal solution is streptomycin/penicillin. After washing the skin sample, incubate with a cellular disintegration proteolytic enzyme, preferably dispase, at a concentration of 1.79-2.00 units/mg under temperature conditions of 4° C. per at least 16-24 hours to obtain a layer of the epidermis and a layer of the dermis. After 16-22 hours, separate the two layers by the use of sterile forceps and place these layers in sterile, independent containers.

Place several strips of dermis from the newborn foreskin or in a sterile container of Petri dish for pre-filling 25% with special medium for endothelial cell growth supplemented with 1% v/v of streptomycin-penicillin 100×, 5%-20% v/v of autogenous serum of the patient and with 0.5-40 ng/ml of endothelial growth factor (VEGF-A) and 0.5-100 ng/ml of VEGF-C; then carefully scrape with a sterile tool sharp pulse with angle at its tip on the dermis strips under sterile conditions to release the microvascular endothelial cells. Subsequently, obtain the Petri dish solution with the released cells and place in a 50 ml falcon tube and centrifuge at 1,500-1,700 revolutions per minute for 5-10 minutes to obtain a microvesicular endothelial cell pellet. Cultivate the pellet in a cell culture flask previously coated with adhesion growth factor for the growth of microvascular endothelial cells.

The same results will be obtained by carefully adding 33.33% of the volume of the special cell culture medium container for mesenchymal stem cells which is supplemented 15-20% v/v of fetal bovine serum to expand donor cells from the foreskin sample of a newborn (allogenic). Optionally, the use of mesenchymal stem cells of spray component 1 is substituted with the use of fibroblasts when placing the dermis layer in a container and mechanically disintegrating with a cutting pulse tool in sterile conditions to obtain pieces of the dermis of a maximum of 1 mm×1 mm, and incubate for a period of at least 10 minutes. Carefully add 33.33% of the container volume of a special cell culture medium for fibroblasts supplemented with 15%-20% v/v of patient autologous serum by the walls of the container and avoid moving the fragments of the dermis and incubate at 37° C., 95% relative humidity, 5% $CO_2$ and 20% $O_2$ for a period of time to obtain monolayer fibroblasts.

Optionally, the use of mesenchymal stem cells of spray component 1 can be substituted with the use of keratinocytes by separating the epidermis layer, placing and washing the epidermis layer in an independent container at least 3 times with the PBS 1× solution, incubating said epidermis layer in a trypsin solution at a concentration of 0.025%-0.05% trypsin in a final volume of ethylenediaminetetraacetic acid (EDTA) for 20 minutes at a temperature of 37° C. to obtain a trypsinized epidermis. Subsequently, neutralize the epidermis with 50% v/v of a culture medium of human keratinocytes containing autologous serum of the patient at 10-20% v/v and shake vigorously for at least 30 seconds to obtain a cellular solution. Subsequently, filter the cell solution with a nitrocellulose filter with a pore size of 40 μm to obtain the human keratinocytes in suspension in the filtrate.

Subsequently, aseptic conditions should be coated on a Petri dish for cell culture with type I collagen at a medical level for 1 hour after sowing the keratinocyte suspension. Wash the Petri dish for cell culture with a 1× phosphate salt solution (PBS) for at least 2 times. Seed the keratinocytes in suspension under aseptic conditions in the Petri dish coated with medical grade type I collagen and add a special cell culture medium for keratinocytes (with epidermal growth factor) supplemented with 15%-20% v/v of autologous serum of the patient and incubate at 37° C., 95% relative humidity, 5% $CO_2$ and 20% $O_2$ for a period of 2 to 4 weeks under aseptic conditions, and change the cell culture medium every second or third day until reaching a confluence 100% for keratinocytes to obtain a greater quantity of monolayer keratinocytes.

Skeletal keratinocytes from the foreskin (allogeneic tissue) can also be planted under aseptic conditions in the Petri dish coated with medical grade type I collagen and a special cell culture medium for keratinocytes (with epidermal growth factor) supplemented with extracellular keratinocytes is added. 15%-20% v/v of fetal bovine serum and incubated at 37° C., 95% relative humidity, 5% $CO_2$ and 20% $O_2$ for a period of 2 to 4 weeks under aseptic conditions.

b) Expand the Monovalent and Monolayer Cells of the Cellular Spraying Compound.

Subsequently, when reaching the confluence of 100% of the primary culture of the mesenchymal cells isolated from the tissues, wash the bottle for cell culture with a phosphate salt solution (PBS) 1× for at least 2 times and incubate for at least 5 minutes with a solution of 0.025%-0.05% trypsin in a final volume of ethylenediaminetetraacetic acid (EDTA) at a temperature of 37° C. to obtain mesenchymal stem cells in suspension; neutralize the trypsinization solution by adding 50% of the volume of the container with cell nutrient culture medium for mesenchymal stem cells, preferably DMEM (Dubeicec modified Eagle medium) high in glucose (4500 mg/L), 25 mM Hepes, supplemented with 1% v/v of streptomycin-penicillin 100×, 10-100% v/v v/v of human autologous serum or supplemented with 10-100% v/v of fetal bovine serum pharmaceutical grade; place 100% of the volume of the mesenchymal stem cells in suspension in a 50 ml Falcon tube and centrifuge at 1,500-1,700 revolutions per minute for 5-10 minutes to obtain a cell pellet from mesenchymal stem cells. Resuspend the cell pellet from the mesenchymal stem cells in 1-10 ml of cell nutrient culture medium for mesenchymal stem cells and in a Neubauer chamber at a 1:1 dilution with methylene blue and re-culture the mesenchymal stem cells at a concentration of 3,000-5,000 cells/cm² in a new jar (bottle) pretreated for the in vitro expansion of monolayer cells; add 33.33%-50% of the container volume of cell nutrient culture medium for mesenchymal stem cells by the walls of the container and incubate at 37° C., 95% relative humidity, 5% $CO_2$ y 20% $O_2$ for a period of time to obtain an amount of $10\text{-}100\times10^6$ of mesenchymal stem cells in monolayer.

Wash the container containing microvascular endothelial cells in monolayer with PBS 1× for at least 2 times and incubate with it at least 5 minutes with a solution of 0025%-0.05% trypsin (recombinant) in a final volume of ethylenediaminetetraacetic acid (EDTA) at a temperature of 37° C. to obtain the microvascular endothelial cells in suspension. Neutralize the trypsinization solution by adding 50% of the volume of the container with cellular nutrient medium of microvessel endothelial cells preferably composed with DME/F-12 medium supplemented with 1%-100% v/v streptomycin-penicillin 100×, 1%-100% v/v of the patient's autogenous serum or 1%-100% v/v of fetal bovine serum, with 0.5-40 ng/ml of endothelial growth factor (VEGF-A) and 0.5-100 ng ml of VEGF-C. Place 100% of the volume of the microvascular endothelial cells in suspension in a 50 ml falcon tube and centrifuge at 1,500-700 rpm for 5 to 10 minutes to obtain a cell pellet of the microvascular endothelial cells. Resuspend the cell pellet of the microvascular endothelial cells in 1-10 ml with cellular nutrient medium of microvessel endothelial cells and count in a Neubauer chamber at a 1:1 dilution with methylene blue and re-culture the microvascular endothelial cells in suspension in a special jar (bottle) for cell expansion previously coated with adhesion growth factor for the growth of microvascular endothelial cells adding 33.33%-50% of the volume of the container with special cell medium for growth of endothelial cells through the walls from the container and incubate at 37° C., 95% relative humidity, 5% $CO_2$ y 20% $O_2$ for a period of time to obtain an amount of $10\text{-}100\times10^6$ micro vessel endothelial cells in monolayer.

Optionally, the use of mesenchymal stem cells can be substituted with the use of fibroblasts and keratinocytes in a 1:1 ratio with the skin microvascular endothelial cells.

Subsequently, wash the container containing the fibroblasts in monolayer with PBS 1× for at least 2 times and incubate for at least 5 minutes with a solution of 0.025%-0.05% trypsin in a final volume of ethylenediaminetetraacetic acid (EDTA) at a temperature of 37° C. to obtain fibroblasts in suspension. Neutralize the trypsinization solution by adding 50% of the volume of the container with special cell culture medium for fibroblasts supplemented with 15-20% v/v of the patient with the autologous serum. Place 100% of the volume of the fibroblasts in suspension in a 50 ml falcon tube and centrifuge at 1,500-1,700 revolutions per minute for 5-10 minutes to obtain a fibroblast cell pellet. Resuspend the cell pellet of fibroblasts in 1-10 ml of special cell culture medium for fibroblasts, count in a Neubauer chamber at a 1:1 dilution with methylene blue and re-sow the fibroblasts in suspension in a special container for the expansion of cells in monolayer, adding 33.33%-50% of volume of the cell culture medium container special for fibroblasts which is supplemented with 15-20% v/v of patient autologous serum through the walls of the container and incubate at 37° C., 95% relative humidity, 5% $CO_2$ and 20% $O_2$ for a period of 10 to $50\times10^6$ of monolayer fibroblasts.

Resuspend, count, and re-culture the fibroblasts in suspension from the prepuce of a newborn in a special container for the expansion of monolayer cells in a spice container for the expansion of cells in monolayer adding 33.33%-50% of the volume of the cell culture medium special for fibroblasts which is supplemented with 15-20% v/v of fetal bovine serum through the walls of the container and incubated at 37° C., 95% relative humidity, 5% CÜ2 20% $O_2$ for a period of time to obtain an amount of $10\text{-}50\times10^6$ of monolayer fibroblasts.

Wash the container containing the monolayer keratinocytes with PBS 1× at least 2 times and incubate for at least 5 minutes with a solution of 0.025%-0.05% trypsin in a final volume of ethylenediaminetetraacetic acid (EDTA) at a temperature of 37° C. Neutralize the trypsinization solution by adding 50% of the volume of the container with special cell culture medium for keratinocytes with epidermal growth factor, supplemented with 15-20% v/v of autologous serum to obtain keratinocytes in suspension. Place 100% of the volume of keratinocytes in suspension in a 50 ml falcon tube and centrifuge at 1,500 revolutions per minute for 5-10 minutes to obtain a cellular keratinocyte pellet.

Resuspend the cell pellet of keratinocytes in 1-10 ml of special cell culture medium for keratinocytes, count in a Neubauer chamber at a 1:1 dilution with methylene blue and re-sow the suspended keratinocytes in a special container for the expansion of cells in monolayer coated with type 1 collagen medical grade adding 33.33%-50% of the volume of the cell culture medium special for keratinocytes with epidermal growth factor, which is supplemented with 15-20% v/v of autologous serum Patient by the walls of the container and incubate at 37° C., 95% relative humidity, 5% $CO_2$ and 20% $O_2$ for a period to obtain a quantity of $10-50\times10^6$ of keratinocytes in monolayer. Resuspend, count, and re-plant the keratinocytes in suspension from the prepuce of a newborn in a special container for the expansion of monolayer cells coated with medical grade type 1 collagen by adding 33.33%-50% of the volume of the spice cell culture medium container for keratinocytes with epidermal growth factor, which is supplemented with 15-20% v/v of autologous serum from the patient through the walls of the container and incubated at 37° C., 95% relative humidity, 5% $CO_2$ and 20% $O_2$ per a period to obtain a quantity of $10-50\times10^6$ of keratinocytes in monolayer.

c) Prepare the Component of the Cellular Spraying Compound.

Centrifuge at 1500-2000 revolutions (rpm) per minute for 5-15 minutes a sample of 5-100 cc of peripheral blood from the patient (autologous tissue) or from a preserved cryo of platelets from a blood bank (allogeneic tissue) with test viral negative preferably collected in a spice tube with sodium citrate anticoagulant, EDTA, destroxa citrate, heparin, to obtain 50% of a heme derived from plasma rich in growth factors.

Wash the container containing mesenchymal stem cells in monolayer with PBS 1× for at least 2 times and incubate for at least 5 minutes with a solution of 0.025%-0.05% trypsin in a final volume of ethylenediaminetetraacetic acid (EDTA) at a temperature of 37° C. to obtain mesenchymal stem cells in suspension. Neutralize the trypsinization solution by adding 50% of the volume of the container with special cell nutrient culture medium for mesenchymal stem cells. Place 100% of the volume of mesenchymal stem cells in suspension in a 50 ml falcon tube and centrifugal at 1,500-1,700 revolutions per minute for 5-10 minutes to obtain a cell pellet with $10-100\times10^6$ of mesenchymal stem cells. Subsequently, resuspend with 5-100 ml of plasma rich in growth factors the cell pellet with $10-100\times10^6$ of mesenchymal stem cells. Subsequently, wash the container containing the monovalent microvascular endothelial cells in 1×PBS for at least 2 times and incubate for at least 5 minutes with a solution of 0.025%-0.05% trypsin in a final volume of ethylenediaminetetraacetic acid (EDTA), at a temperature of 37° C. Neutralize the trypsinization solution by adding 50% of the volume of the container with cell nutrient culture medium for endothelial cells to obtain microvascular endothelial cells in suspension.

Place 100% of the volume of the microvascular endothelial cells in suspension in a 50 ml falcon tube and centrifugal at 1,500-1,700 revolutions per minute for 5-10 minutes to obtain a pellet with $10-100\times10^6$ of microvascular endothelial cells. Subsequently, resuspend or mix the pellet of endothelial cells in suspension with 5-10 Gml of plasma rich in growth factors.

Fill in a syringe with 1-100 ml of the cell spray solution containing $10-100\times10^6$ of resuspended mesenchymal stem cells in the plasma rich in growth factors. Subsequently, fill in a second syringe with 1-100 ml of the cell spray solution containing $10-100\times10^6$ microvascular endothelial cells resuspended in the plasma rich in growth factors.

Similar results are obtained if it is filled in a third syringe with 1-100 ml of plasma rich in growth factors containing $10-100\times10^6$ mesenchymal stem cells mixed with 10-10 G×$10^6$ microvascular endothelial cells. Also, better results are obtained by filling in a syringe with 1-100 ml of the cell spray solution containing $10-100\times10^6$ of mesenchymal stem cells resuspended in the plasma rich in growth factors and mixing with collagen type 1 medical grade at a concentration of 1-5 mg/ml at a ratio of 1:1 between both solutions. Subsequently fill in a second syringe with 1-100 ml of the cell spray solution containing $10-100\times10^6$ microvascular endothelial cells resuspended in the plasma rich in growth factors with collagen type 1 medical grade at a concentration of 1-5 mg/ml at a ratio of 1:1 between both solutions.

Similar results are obtained if it is filled in a third syringe with 1-100 ml of plasma rich in growth factors and mixed with type 1 collagen medical grade at a concentration of 1-5 mg/ml at a ratio of 1:1, containing $10-100\times10^6$ mesenchymal stem cells and $10-100\times10^6$ microvascular endothelial cells.

Better results are obtained by filling in a syringe with 1-100 ml of the cell spray solution containing $10-100\times10^6$ mesenchymal stem cells resuspended in the plasma rich in growth factors with medical grade hyaluronic acid to a concentration of 1-5 mg/ml at a ratio of 1:1 between both solutions. Subsequently fill in a second syringe with 1-100 ml of the cell spray solution containing $10-100\times10^6$ microvascular endothelial cells resuspended in the plasma rich in growth factors with medical grade hyaluronic acid at a concentration of 1-5 mg/ml at a ratio of 1:1 between both solutions. Similar results are obtained if it is filled in a third syringe with 1-100 ml of plasma rich in growth factors with medical grade hyaluronic acid at a concentration of 1-5 mg/ml at a ratio of 1:1, containing $10-100\times10^6$ of mesenchymal stem cells and $10-100\times10^6$ microvascular endothelial cells.

Optionally, the cellular spraying compound can be mixed with the microvascular endothelial cells with fibroblasts and keratinocytes in a 1:1 ratio in substitution of the mesenchymal stem cells by washing with 1×PBS, the container containing the monolayer fibroblasts and monolayer keratinocytes by at least 2 times and incubate for at least 5 minutes with a solution of 0.025%-0.05% trypsin in a final volume of ethylenediaminetetraacetic acid (EDTA) at a temperature of 37° C. to obtain a fibroblasts in suspension. Neutralize the trypsinization solution by adding 50% of the volume of the container with special cell culture half for fibroblasts and supplementary keratinocytes with 15-20% v/v of the patient's autologous serum. Place 100% of the volume of the fibroblasts and keratinocytes in suspension in a 50 ml falcon tube and centrifugal at 1,500-1,700 revolutions per minute during 5-10 minutes, to obtain a cell pellet with $10-100\times10^6$ of fibroblasts and $10-100\times10^6$ of keratinocytes.

Subsequently, resuspend with 5-20 ml of plasma rich in growth factors the cell pellet with $10-100\times10^6$ fibroblasts and $10-100\times10^6$ keratinocytes.

Fill in a syringe with 1-100 ml of the cell spray solution containing $10-100\times10^6$ fibroblasts and $10-100\times10^6$ keratinocytes in the plasma rich in growth factors. Subsequently, fill in a second syringe with 1-100 ml of the cell spray solution containing $10-100\times10^6$ microvascular endothelial cells resuspended in the plasma rich in growth factors.

Similar results are obtained if it is filled in a third syringe with 1-100 ml of plasma rich in growth factors containing 10-100×10$^6$ fibroblasts and 10-100×10$^6$ keratinocytes mixed with 10-100×10$^6$ of microvascular endothelial cells.

Also, better results are obtained by filling in a syringe with 1-100 ml of the cell spray solution containing 10-100×10$^6$ of fibroblasts and 10-100×10$^6$ of resuspended keratinocytes in the rich plasma in growth factors and mix with collagen type 1 medical grade at a concentration of −5 mg/ml at a ratio of 1:1 between both solutions. Subsequently fill in a second syringe with 1-100 ml of the cell spray solution containing 10-100×10$^6$ microvascular endothelial cells resuspended in the plasma rich in growth factors with collagen type 1 medical grade at a concentration of 1-5 mg/ml at a ratio of 1:1 between both solutions. Similar results are obtained if it is filled in a third syringe with 1-100 ml of plasma rich in growth factors and mixed with collagen type 1 medical grade at a concentration of 1-5 mg/ml at a ratio of 1:1, containing 10-100×10$^6$ fibroblasts, 10-100×10$^6$ keratinocytes and 10-100×10$^6$ microvascular endothelial cells.

Better results are obtained by filling in a syringe with 1-100 ml of the cell spray solution containing 10-100×10$^6$ fibroblasts and 10-100×10$^6$ of resuspended keratinocytes in the factor-rich plasma of growth with medical grade hyaluronic acid at a concentration of 1-5 mg/ml at a ratio of 1:1 between both solutions. Subsequently fill in a second syringe with 1-100 ml of the cell spray solution containing 10-100×10$^6$ microvascular endothelial cells resuspended in the plasma rich in growth factors with medical grade hyaluronic acid at a concentration of 1-5 mg/ml at a ratio of 1:1 between both solutions.

Similar results are obtained if it is filled in a third syringe with 1-100 ml of plasma rich in growth factors with medical grade hyaluronic acid at a concentration of 1-5 mg/ml at a ratio of 1:1, containing 10-100×10$^6$ of fibroblasts, 10-100×10$^6$ of keratinocytes and 10-100×10$^6$ microvascular endothelial cells.

d) Prepare the Component With the Compound of the Cross-Linking Agent or Reaction of the Cellular Spraying Compound.

Generate under aseptic conditions—100 ml of human thrombin from medical grade donor, at a concentration of 1-20 U/ml in sodium chloride at 0.9% v/v and 1 ml of $CaCl_2$ at 1-3% w/v to obtain 10-100 ml of the cross-linking and reaction agent solution; subsequently loading the reaction cross-linking agent into a syringe to obtain the reaction cross-linking agent of the cellular spray solution.

The same results can be obtained when 10-100 ml of human thrombin from a medical grade donor is generated under aseptic conditions at a concentration of 1-20 U/ml v/v in sodium chloride at 0.9% v/v and 1 ml of $CaCl_2$ al 1-3% w/v to obtain 10-20 ml and 10 mg/ml w/v of an antifibrinolytic such as tranexamic acid or aprotonin to obtain the solution of the cross-linking and reaction agent; subsequently loading the reaction cross-linking agent into a syringe to obtain the reaction cross-linking agent of the cellular spray solution.

The same results can be obtained if a solution of CaC at a concentration of 1-3% w/v in sodium chloride at 0.9% v/v is prepared under aseptic conditions and loaded into a syringe to obtain 5-100 ml of the reactive cross-linking agent of the cell spray solution.

The same result can be obtained by generating in aseptic conditions 10-20 ml of donor human thrombin from the product called "Tissucol" (Baxter allogeneic fibrinogen) by diluting it in 0.9% v/v sodium chloride to obtain a concentration of 20 U/ml and 1 ml of $CaCl_2$ at 1-3% w/v to obtain 1-100 ml of the solution of the cross-linking and reaction agent; subsequently loading the reaction cross-linking agent into a syringe to obtain the reaction cross-linking agent of the cellular spray solution.

The same result can be obtained by generating in aseptic conditions 10-100 ml of bovine thrombin of lung at a concentration of 1-20 U/ml in sodium chloride at 0.9% v/v and 1 ml of $CaCl_2$ at 1-3% w/v to obtain 10-100 ml of the solution of the cross-linking agent and of reaction; subsequently loading the reaction cross-linking agent into a syringe to obtain the reaction cross-linking agent of the cell spray solution.

DETAILED DESCRIPTION OF THE APPLICATION METHOD

The present invention relates to a process of production, application and care of a cellular spraying compound of mesenchymal stem cells and microvascular endothelial cells resuspended in a regenerative solution to generate a therapeutic treatment of skin lesions; which is based on the implantation of mesenchymal stem cells that can be substituted by the use of fibroblasts and keratinocytes in a 1:1 ratio and microvascular endothelial cells of human origin pre-expanded in vitro for 4-8 weeks under sterile conditions total with minimum sterility classification and the manufacture of the implantation vehicle that forms the regenerative solution of cellular implantation with its respective care for the total re-epithelization of total or partial thickness skin lesions, which comprises the following stages:

a) Preparation and Transport of the Cellular Aspersion Compound and its Regenerative Solution to the Operating Room.

Under aseptic conditions, mesenchymal stem cells and microvascular endothelial cells are centrifuged both in suspension contained in the falcon tube of 50 ml at 1,500-1,700 revolutions per minute per 5-10 minutes to obtain a pellet with 10-100×10$^6$ of the mesenchymal stem cells and microvascular endothelial cells. Subsequently, decant the supernatant of both tubes, add 1 ml of cellular nutrient culture medium for mesenchymal stem cells and microvascular endothelial cells, saline or PBS 1× and place both tubes separately in a cooler with a temperature of 4 degrees Celsius. Subsequently, transport the cooler to the operating room or keep refrigerated at 4 degrees centigrade for its application.

Good results are also obtained if centrifuged at 1,500-1,700 revolutions per minute the mesenchymal stem cells and microvascular endothelial cells in suspension contained in the 50 ml falcon tube for after 5-10 minutes to obtain a pellet with 10-100×10$^6$ of both cells. Subsequently, decant the supernatant of both tubes and add to both pellets 1 ml of cell culture medium and 5-10 ml of medical grade I collagen type at a concentration of 1-3 mg/ml; place both tubes in a cooler with ice to maintain 4 degrees Celsius and transport the cooler to the operating room at 4 degrees Celsius.

It can also be kept in refrigeration of 4 degrees Celsius for its application. Also, good results are obtained if centrifuged mesenchymal stem cells and microvascular endothelial cells in suspension in contents in the Falcon tube of 50 ml then decant the supernatant of both tubes and resuspend both pellets with 1 ml of nutritious cell culture medium and resuspend, adding with 1-10 ml of medical grade hyaluronic acid at a concentration of 1-3 mg/ml and place both tubes in a cooler with ice to maintain at 4 degrees centigrade. Subsequently, transport the cooler to the operating room or keep it in refrigeration for a period of time.

Optionally, the use of mesenchymal stem cells can be substituted with the use of fibroblasts and keratinocytes in a 1:1 ratio where, under aseptic conditions, fibroblasts and keratinocytes are centrifuged both in suspension contained in the falcon tube from 50 ml to 1,500-1,700 revolutions per minute for after 5-10 minutes to obtain a pellet with $10\text{-}100\times 10^6$ fibroblasts and with $10\text{-}100\times 10^6$ of keratinocytes. Afterward, decant the supernatant of both tubes, add 1 ml of medium cell culture nutrient fibroblasts, and keratinocytes, and place both tubes separately in a cooler with a temperature of 4 degrees Celsius. Subsequently, transport the ice chest to the operating room or keep refrigerated at 4 degrees Celsius for its application.

Good results are also obtained if the fibroblasts and keratinocytes in suspension contained in the falcon tube of 50ml are centrifuged at 1,500-1,700 revolutions per minute for 5-10 minutes to obtain a pellet with $10\text{-}100\times 10^6$ of both cells. Subsequently, decant the supernatant of both tubes and add to both pellets 1 ml of cell culture medium and with 5-10 ml of medical grade I collagen type at a concentration of 1-3 mg/ml; place both tubes in a cooler with ice to maintain 4 degrees Celsius and transport the cooler to the operating room at 4 degrees Celsius.

It can also be kept in refrigeration of 4 degrees Celsius for its application.

b) Transport of the Reticulate Agent Reaction Piece of the Spray Solution.

Subsequent to the preparation under aseptic conditions of the reaction cross-linking agent of the reaction solution, the syringe of 5-10 c duly covered and sealed, is placed in the same cooler that contains the cellular spray compound at 4 degrees and both are transported Compound to the operating room or kept in cooling by ? after a while.

c) Total Regenerative Solution Preparation of the Spray Compound.

Under aseptic conditions in the operating room, obtain in a special tube with sodium citrate anticoagulant a sample of 1-100 cc of peripheral blood coming from the patient (autologous tissue) to be treated with the cellular aspersion compound and centrifuge at 1,500-2,000 revolutions (rpm) per minute for after 5-15 minutes to get 1-100 ml of plasma rich in growth factors (blood acellular plasma). Subsequently, obtained through a syringe and under aseptic conditions the plasma rich in growth factors and resuspend it with both tubes in refrigeration containing the mixture of microvascular endothelial cells and mesenchymal stem cells to prepare the total solution of the cellular aspersion compound.

Better results are obtained if the plasma rich in growth factors of the patient is resuspended with the microvascular endothelial cells, mesenchymal stem cells and the medical grade type I collagen solution at a concentration of 1-100 mg/ml to prepare the total solution composed of cellular spray.

Better results are obtained if the plasma rich in growth factors of the patient is resuspended with the microvascular endothelial cells, mesenchymal stem cells, and the medical grade hyaluronic acid solution at a concentration of 1-100 mg/ml to prepare the total compound solution of cellular aspersion.

d) Load the Medical Spray Device for Sprinkling/Spraying and Connection to Your Power Supply.

In aseptic conditions in the office and/or in the ambulatory operating room, the medical spray device is loaded with two syringes with the syringe of the cell spray compound containing both cells together or separately with the regenerative solution and the second syringe with the agent compound reaction cross-linker of the cellular spray solution.

Connect the medical spray device to the compressed air regulator unit and set the pressure to 20-25 psi/1.75 bar for fine drops and 10-15 psi/1 bar for thick spray drops. Connect a tank, power supply or medical grade compressed air supply to the compressed air regulating unit.

e) Application of the Cellular Spraying Compound of Mesenchymal Stem Cells or Keratinocytes or Fibroblasts and Microvascular Endothelial Cells and Their Regenerative Solution.

Place the medical spray device at a distance of not less than 3 cm above the surface of the skin lesion, open the source of compressed air and push the plunger of both syringes at the same time for the spraying of the mesenchymal stem cells and the endothelial cells separately or previously mixed micro-vents and mechanically distributing the cellular spray compound over the wound to form a gel filler or surface film on said wound.

When the wound is superficial, the method of application of a cellular spraying compound is based only on the implantation of $10\text{-}100\times 10^6$ mesenchymal stem cells evenly distributed over the cutaneous lesion. When the wound is deep, the application method of a cellular spraying compound is based on the implantation of $10\text{-}100\times 10^6$ of mesenchymal stem cells and $10\text{-}100\times 10^6$ of microvascular endothelial cells evenly distributed over the skin lesion filling the stroma, the base layer and the epithelial layer of the skin lesion. This application can be based on 1 single application or in various applications to fill the defect of total thickness (deep) or surface. Or in turn, in the course of time for skin tissue regeneration. In addition to this, the cellular amount will depend on the injury or injury of the wound.

Optionally it can be replaced by use of mesenchymal stem cells with the use of fibroblasts and keratinocytes in a 1:1 ratio.

f) Bandage and Protection of the Cellular Spraying Compound of Mesenchymal Stem Cells and Endothelial Cells and Their Regenerative Solution.

After implantation, aseptic conditions place triple antibiotic cream on the contour of the filled wound and the cellular spraying compound and place sterile gauze, a silicone film on the sterile gauze and finally bandage the wound.

Example 1

Preferential Mode Use of the Cellular Aspersion Composite of Microvascular Endothelial Cells and Human Mesenchymal Stem Cells on Skin Injuries To carry out the sprinkling and/or spraying of the cellular spraying compound of mesenchymal stem cells and human microvascular endothelial cells resuspended in the regenerative solution, the syringe of the cellular spraying compound containing both cells together or separately is adapted under aseptic conditions with the platelet-rich plasma and at the same time and in a second conduit in the medical device the syringe is adapted with the compound of the reaction cross-linking agent of the cellular spray solution so that both molecules interact with each other at the time of spraying in the air. Subsequently, connect the medical spray device to the compressed air regulator unit and set the pressure to 20-25 psi/1.75 bar for fine drops and 10-15 psi/1 bar for thick drops. Connect a medical grade tank, power supply or compressed air supply to the compressed air regulator unit. Connect the FibriJet or any other medical sprinkler/sprayer device at a distance of not less than 3 cm above the surface of the tissue, open the source of compressed air and push the plunger of both syringes at the same time for the spraying of the mesenchymal stem cells and microvascular endothelial cells separately in different syringes or previously mixed in the total regenerative solution.

The cellular spraying compound of mesenchymal stem cells and autologous and/or donor microvascular endothelial cells is composed of a cell spray solution and a solution of cross-linking agent of reaction of the cell spray solution that at the time of pressure spraying both molecules will be combined to encapsulate the living cells which will be deposited on the surface of the tissue and will form on this a film and/or gel-filled filling with living cells in its interior for the generation of new extracellular matrix and promote an early vascularization to the new tissue by means of microvascular endothelial cells.

When the cutaneous wound is superficial, that is to say, superficial burn of first, second or third degree, as well as the diabetic ulcer where the damaged tissue is only the epidermis of the skin, the method of application of a cellular spraying compound is based only in the implantation of $10\text{-}100 \times 10^6$ of mesenchymal stem cells uniformly distributed over the cutaneous lesion to promote a rapid re-epithelialization of the epidermis by stimulating the production of new keratin on the wound surface by implanting the stem cells mesenchymal. However, the application will be only once or in various applications along with the cellular amount, depending on the degree of the injury.

When the wound is deep, that is to say, deep burn of first, second or third degree, as well as deep diabetic ulcer where the damaged tissue is not only in the epidermis if there is no damage to the dermal layer (dermis) of the skin as well as reconstruction of cutaneous tissue as a result of trauma or removal of said tissue by cancer, reconstruction and regeneration is based on a method of application by implantation of $10\text{-}100 \times 10^6$ mesenchymal stem cells for differentiation of the 3 tissue layers and $10\text{-}100 \times 10^6$ of microvascular endothelial cells evenly distributed over the skin lesion to promote early angiogenesis of the new tissue formed. However, the application will be only once or in various applications along with the cellular amount, depending on the degree of the injury.

Optionally the cellular spraying compound of mesenchymal stem cells and microvascular endothelial cells is prepared 15-25% v/v of a solution composed of 225-100 grams/ml of bovine blood fibrinogen dissolved in phosphate buffered saline at a concentration of 1×.

Optionally, the use of mesenchymal stem cells can be substituted with the use of fibroblasts and keratinocytes in a 1:1 ratio.

Example 2

Invention Preferential Mode

The cellular spraying compound of mesenchymal stem cells and autologous and/or donor microvascular endothelial cells is composed of a cellular spraying solution and a solution of cross-linking agent of reaction of the cellular spraying solution which at the time of pressure spraying they combine both molecules to encapsulate the living cells which will be deposited on the surface of the tissue and form a film and/or gel filler with living cells in their interior for the generation of a new extracellular matrix.

The implanted cells of the cellular spraying compound are healthy donor cells (allogeneic) obtained from adipose tissue, peripheral blood, bone marrow, amniotic fluid, dental pulp and foreskin of a newborn and/or own patient to treat (autologous) from a sample of adipose tissue, peripheral blood, bone marrow, amniotic fluid, dental pulp and skin of the patient. These cells are mesenchymal stem cells isolated from adipose tissue, peripheral blood, bone marrow, amniotic fluid, dental pulp and microvascular endothelial cells are isolated from a skin sample; which are pre-expanded in vitro for 2-4 weeks in order to obtain $10\text{-}100 \times 10^6$ of mesenchymal stem cells and $10\text{-}100 \times 10^6$ of microvascular endothelial cells. Subsequently, the regenerative solution of this aspersion compound is prepared from a plasma rich in growth factors of patient to be treated, which is obtained by centrifuging a sample of blood of a said patient in the operating room prior to the application of the cellular spraying compound, subsequently combining with either type I collagen and hyaluronic acid at a ratio of 1:1 and resuspending the cells which are transported to operating room in ice cooler to keep them at 4 C in a latency state. The result of this combination of elements to form the regenerative solution results in the easy spraying of the cells on the wound and a formation/filling of a gelling layer on the skin lesion. Said gelled or polymerized layer has the function of transporting, protecting, encapsulating, facilitating and especially potentiating (providing growth factors) the cellular effect of the mesenchymal stem cells and the microvascular endothelial cells implanted on the skin lesion.

Therefore, the therapeutic application of all the components of this cellular spraying compound and its regenerative solution potentiates the treatment of the implanted cells by means of the formation of new healthy tissue promoting a rapid re-epithelization, prompt neovascularization, and regeneration of the cutaneous wound in a short time lapse.

In turn, the use of this technology results in the null formation of fibrotic tissue and muscle contraction in the recovery of the lesion, so we can affirm that the tissue is regenerating and not healing.

Also, we can affirm that the regeneration of the new cutaneous tissue from this technology, promotes the recovery of its functionality from the new migration of Sos melanocytes in the re-epithelialized zone and the formation of new hair follicles for the generation of hair.

Example 3

Manipulation Mode of the Cellular Aspersion Compound

Under operating conditions, the cell aspersion process is carried out, which consists of 2 solutions sprayed at the same time by mechanical pressure of both pistons of both syringes of a medical spray device (FibriJet-Micromedics gas applicator) supplied at all times with air medical grade tablet for the purpose of generating a gelling and/or filling film on the wound or skin lesion with live cells encapsulated as re-epithelization treatment.

The medical device (FibriJet-Micromedics gas applicator) will contain two syringes (5 cc) with the two solutions to be reacted: cell spray solution (fibrinogen, mesenchymal stem cells, and microvascular endothelial cells) and the solution of the reaction cross-linking agent (thrombin) of the cell spray solution.

Spraying will be done directly on the skin wound at least 3 cm away through the medical device (FibriJet-Micromedic gas applicator) connected to a supply of compressed air. The pressure required to exert the spray will be 20-25 PSI/1.75 bar of compressed air that will push the two syringes and spray their contents with fine drops on the wound obtaining a fibrin-containing fibrin film containing mesenchymal stem cells and microvascular endothelial cells that will promote the production of the new extracellular matrix on the wound. In order to obtain thick drops spraying process, the spray will be 10-15 PSI/1.0 bar of compressed air. Therefore, this process will provide a re-epithelialization of the wound in a short time, a reorganization of the tissue, early neovascularization and complete regeneration of the lesion avoiding exposure to infections.

The cellular spraying compound of mesenchymal stem cells and of microvascular endothelial cells which are in contact with the skin lesion will, over time, provide re-epithelialization and a more rapid regeneration by the addition of the live mesenchymal stem cells embedded within it. This network of fibrin (human fibrinogen, human acellular plasma, bovine fibrinogen) stimulating a new generation of extracellular matrix and collagen fibers.

Under operating conditions, the cell aspersion process is performed by simultaneously spraying 2 solutions through a medical device (FibriJet-Micromedics gas applicator) to generate a chemical film and/or filler on the wound or skin lesion as a re-epithelialization treatment. and potentiating skin regeneration by encapsulating living cells over the gelling film. Subsequently, the antibiotic triple cream is applied aseptically on the contour of the filled wound and the cellular spraying compound, sterile gauzes are placed, a Tegaderm on the sterile gauzes and finally bandaging the wound, which is performed a change of bandage each 3rd day.

Optionally, the use of mesenchymal stem cells can be substituted with the use of fibroblasts and keratinocytes in a 1:1 ratio.

Example 4

Preference Use of the Invention

Under operating room conditions, the cell spray process is carried out, which consists of 2 solutions sprayed at the same time by a medical device (FibriJet-Micromedics gas applicator) to generate a gelling film and/or filler on the wound or cutaneous lesion with cells living cells encapsulated as re-epithelization treatment.

The implanted cells are healthy donor cells (allogenic/autologous) expanded in vitro from newborn prepuces and autologous cells from the same patient. The purpose is to promote a rapid re-epithelialization and regeneration of wounds or skin lesions. This therapeutic process is mainly focused on the treatment of the following pathologies:

$1^{st}$, $2^{nd}$, and $3^{rd}$ grade surface burns.
$1^{st}$, $2^{nd}$, and $3^{rd}$ grade deep burns.
Venous ulcers of the leg and ulcers due to venous stasis.
Any traumatic pathology reconstruction or skin loss. (Breast reconstruction, forearms, legs, thighs, etc.)

The invention claimed is:

1. A process for obtaining a spraying compound of skin microvascular endothelial cells comprising:
   a) isolating 1) the mesenchymal stem cells or a combination of fibroblasts and keratinocytes in a 1:1 ratio, and 2) the skin microvascular endothelial cells from a tissue containing the cells;
   b) expanding the isolated cells in a monolayer;
   c) washing at least two times the monolayer with a phosphate salt solution (PBS) containing 10% v/v of an antibiotic or an antifungal agent;
   d) washing at least two times the monolayer of step c) with a PBS solution containing 1% v/v of an antibiotic or an antifungal agent;
   e) reacting the monolayer of step d) with a reaction cross-linking agent to obtain a cellular aspersion compound; and
   f) loading the cellular aspersion compound into an aspersion device.

2. The process according to claim 1, wherein the mesenchymal stem cells are chosen from the group consisting of an adipose tissue, a blood tissue, an amniotic fluid, and a dental pulp, wherein the blood tissue is selected from the group consisting of a peripheral blood, a bone marrow, and an umbilical cord blood; wherein the microvascular endothelial cells are selected from the group consisting of a prepuce of a newborn and a sample of adult skin; and wherein the fibroblast and keratinocytes are selected from the group consisting of a foreskin of a newborn and a sample of an adult skin.

3. The process according to claim 2, wherein the antibiotic or the antifungal agent is selected from streptomycin or penicillin.

4. The process according to claim 2, wherein when the mesenchymal stem cells are isolated from the dental pulp of an extracted tooth, the extracted tooth is placed in a mixture of an enzyme solution of 4 mg/mL type IA collagenase and 2 mg/mL of dispase in a 1:1 ratio for 60 minutes at 37° C., then filtered through a 70 μm cell filter, the resulting cell suspension is centrifuged for 8 minutes at 1,500-1,700 rpm and then suspended in a cell nutrient medium having 4500 mg/L of glucose, and 25 mM of Hepes.

5. The process according to claim 2, wherein when the mesenchymal stem cells are extracted from the amniotic fluid, 5-100 cc of the amniotic fluid from a 16th-week gestation is centrifuged at 1500-2000 rpm for at least 5 minutes in sterile conditions, then after the centrifugation the supernatant is decanted, and then under sterile conditions, pellets are suspended with at least 5 ml of a nutrient medium for amniotic fluid cells containing DME-alpha (Dulbecco's modified Eagle medium-alpha) supplemented with amino acid L-Glutamine, a patient serum, streptomycin-penicillin 100×, a medium Chang B®, and a medium Chang C®.

6. The process according to claim 2, wherein the microvascular endothelial cell is obtained by placing several strips of dermis in a sterile container on a petri dish filled with a medium for endothelial cell growth supplemented with an autologous serum of the patient and with endothelial growth factor (VEGF-A) and 0.5-100 ng/ml of VEGF-C, the strips of the dermis are scraped from a foreskin or skin sample with a sterile cutting pulse tool with a tip having an angle under sterile conditions.

7. The process according to claim 1, wherein in the step b) the isolated mesenchymal stem cell is washed with a phosphate salt solution (PBS) at least 2 times and incubated for at least 5 minutes with an ethylenediamine-tetraacetic acid (EDTA) solution including 0.025%-0.05% of trypsin at a temperature of 37° C. to obtain mesenchymal stem cells in suspension; then neutralized by adding 50% of the volume of the container with a cell culture medium modified with 4500 mg/L of glucose, and 25 mM of Hepes, supplemented with 10-40% v/v of a patient serum or supplemented with 10-40% v/v of a pharmaceutical grade fetal bovine serum.

8. The process according to claim 1, wherein in the step c) the monolayer is washed with PBS at least 2 times and incubated for at least 5 minutes with an ethylenediaminetetraacetic acid (EDTA) solution including 0.025%-0.05% of trypsin at a temperature of 37° C. to obtain mesenchymal stem cells in suspension; then the suspension is neutralized by adding 50% of the volume of the container with a cell culture medium for supplementary mesenchymal stem cells with a patient serum or supplemented with a pharmaceutical grade fetal bovine serum; the suspension is placed in a falcon tube and centrifuged at 1,500-1,700 revolutions per minute for 5-10 minutes to obtain a cell pellet.

9. The process according to claim 1, wherein in the step e) the reaction cross-linking agent is thrombin and the thrombin is generated by:

a solution comprising a human thrombin at a concentration of 11-100 U/ml in sodium chloride at 0.9% v/v, 1 ml of $CaCl_2$) at 1-3% w/v, and 1-10 mg/ml w/v of an antifibrinolytic, the antifibrinolytic is selected from the group consisting of a tranexamic acid and an aprotonin to obtain 10 to 100 ml of the solution of the thrombin; or an aqueous solution comprising a human thrombin and $CaCl_2$ at a concentration of 1-3% w/v in 0.9% v/v sodium chloride; or solution comprising 10-100 ml of a human thrombin diluted in sodium chloride at 0.9% v/v to obtain a concentration of 5-20 U/ml and 1 ml of $CaCl_2$) at 1-3% w/v to obtain 10-100 ml of the thrombin and reaction agent solution; or a solution comprising 10-20 ml of thrombin, from bovine lungs, at a concentration of 10-20 U/ml in sodium chloride at 0.9% v/v, and 1 ml of $CaCl_2$) at 1-3% w/v to obtain 10-100 ml of the solution of a foaming agent.

10. A method for applying the spraying compound of claim 1 to a cutaneous lesion on a patient, the method comprising the following steps:

charging a medical spray device for sprinkling/spraying with the cellular aspersion compound inside the aspersion device;

applying the cellular spraying compound to the cutaneous lesion on the patient; and bandaging and protecting the area of the patient where the cellular spraying compound was applied.

11. The application method according to claim 10, wherein the mesenchymal stem cells and the skin microvascular endothelial cells are centrifuged by spin-dry at 1,500-1,700 revolutions per minute for 5-10 minutes.

12. The application method according to claim 10, wherein in the step applying the spraying compound, the medical spraying device is placed at a distance of not less than 3 cm above the surface of the cutaneous lesion; the cellular spraying compound is mechanically distributed over the cutaneous lesion to form a gelling film on said cutaneous lesion; sterile gauzes are placed on the cutaneous lesion containing the cellular spraying compound; a silicone film is placed on the sterile gauze to prevent drying of the cutaneous lesion and loss of water and a general bandage is placed on the silicone film to protect the cellular spraying compound.

13. The application method according to claim 12, further including the step of applying triple antibiotic cream on a contour of the cutaneous lesion treated with the cellular aspersion compound prior to the step of bandaging and protecting the area of the patient.

* * * * *